United States Patent [19]

Doherty et al.

[11] Patent Number: 4,989,594
[45] Date of Patent: Feb. 5, 1991

[54] ATHLETIC SUPPORTER HAVING IMPROVED PROTECTIVE CUP RETAINING MEANS

[75] Inventors: Sara J. Doherty, Franklin; William Litchfield, Sanbornton, both of N.H.

[73] Assignee: Star Specialty Knitting Co., Inc., Laconia, N.H.

[21] Appl. No.: 63,117

[22] Filed: Jun. 17, 1987

[51] Int. Cl.$^5$ .................................................. A61F 5/40
[52] U.S. Cl. ...................................... 128/158; 128/160; 2/247; 2/252
[58] Field of Search .................... 128/96, 99, 100, 101, 128/102, 158, 159, 160, 161, 162, ; 2/401, 403, 2, 78 B, 78 C, 78 D, 252, 247, 250; 66/176

[56] References Cited

U.S. PATENT DOCUMENTS

| | | | |
|---|---|---|---|
| 1,390,086 | 9/1921 | Clements | 2/78 C |
| 1,588,066 | 6/1926 | Thorp | 128/160 |
| 2,266,062 | 12/1941 | Montmarquet | 128/160 |
| 2,283,684 | 5/1942 | Matthews | 128/138 R |
| 2,825,068 | 3/1958 | Montgomery | 2/247 |
| 3,176,686 | 4/1965 | Barnes | 128/158 X |
| 3,621,846 | 11/1971 | Lehman | 128/160 X |
| 3,788,314 | 1/1974 | Noreen | 2/2 X |
| 3,880,160 | 4/1975 | Hall | 128/158 |
| 4,134,400 | 1/1979 | Dimatteo | 128/158 |
| 4,145,763 | 3/1979 | Abrams et al. | 2/403 |
| 4,453,541 | 6/1984 | Castelli et al. | 128/158 |
| 4,549,315 | 10/1985 | English et al. | 2/2 |
| 4,561,121 | 12/1985 | Ehring et al. | 2/2 |
| 4,669,125 | 6/1987 | Allen | 2/252 X |

Primary Examiner—Robert A. Hafer
Assistant Examiner—Kevin G. Rooney
Attorney, Agent, or Firm—Stephen G. Matzuk

[57] ABSTRACT

An athletic supporter having a pouch adapted to receive and retain a protector cup through an aperture at a peripheral edge, and having a member overlapping the aperture for retaining the protector cup therein when the athletic supporter is worn.

8 Claims, 2 Drawing Sheets

ATHLETIC SUPPORTER HAVING IMPROVED PROTECTIVE CUP RETAINING MEANS

FIELD OF THE INVENTION

The present invention relates to athletic supporters and, more particularly, to athletic supporters retaining body protective elements therein.

BACKGROUND OF THE INVENTION

Athletic supporters including a front panel typically include an additional panel expandable to form a volume to receive and retain a body protector cup therein. The protector cup, being received by the pouch, is retained by straps secured by clips, Velcro (TM) closures or other supplemental mechanical devices. However, these closure elements typically comprise a material of substantially different characteristics than the pouch material to which it is attached. As the article is worn and stressed, or as the material wears and ages, the differences between the materials cause the portion of the pouch to which the closures are secured, or the closures themselves, to fatigue, tear, degrade or otherwise become inoperative, permitting the protective cup to become dislodged, creating an inconvenience and potentially subjecting the user to a risk of injury.

SUMMARY OF THE INVENTION

The athletic supporter of the present invention includes a pouch having a front and back panel having an aperture at the top, wherein the front panel extends over and down the rear panel covering the aperture, being secured at the outward edges to the panel. Thus, the aperture is occluded, permitting a protective cup to be retained therein. As the article is worn, the stresses created within the structural design of the pouch area retain the cup therein without the need of auxiliary or supplemental closure devices. Furthermore, the occlusion of the aperture by substantially the same material as the rest of the pouch and the retention of the pouch to the elastic support in a uniform manner permit the article to be stressed in use without inducing premature fatigue of the material at the points of closure and retention, in response to the stress imposed, to retain the protective cup therein.

BRIEF DESCRIPTION OF THE DRAWING

These and other features of the present invention will be better understood by reading the following detailed description taken together with the drawing wherein.

DETAILED DESCRIPTION OF THE INVENTION

Figure 1:
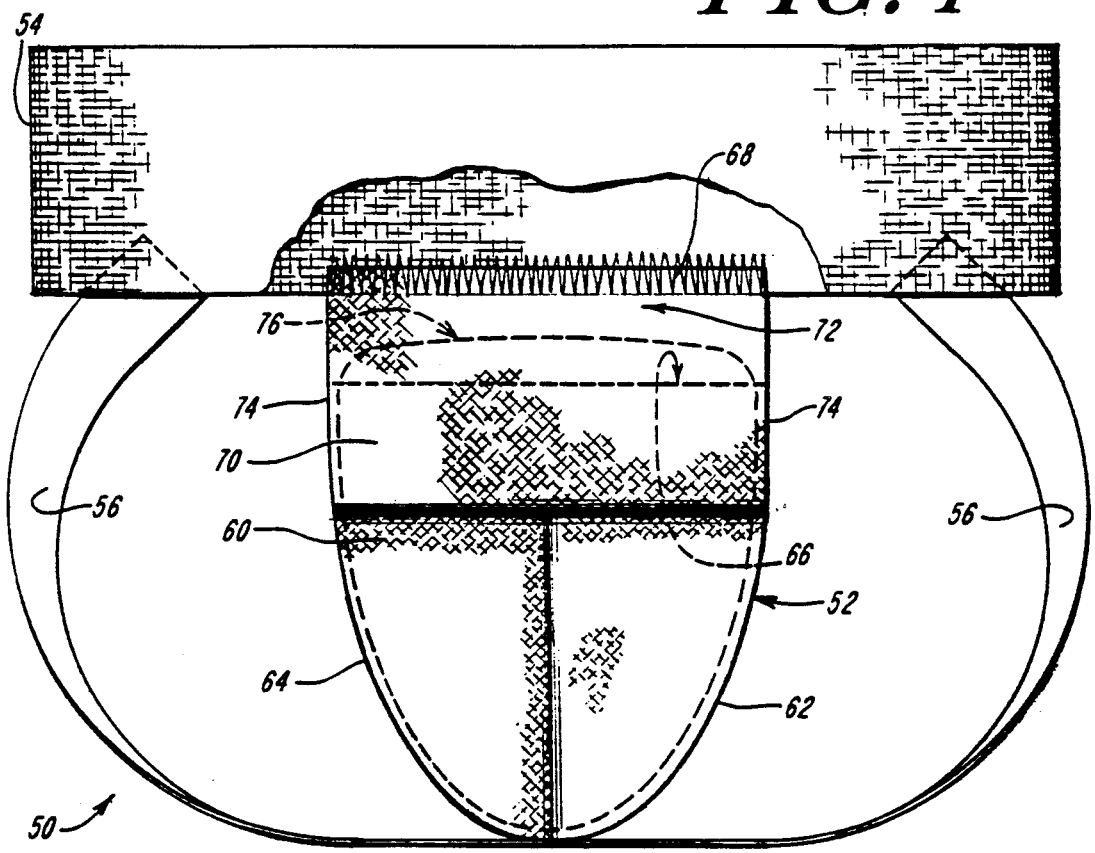
FIG. 1 is a rear view of one embodiment of the athletic supporter according to the present invention.
Figure 2:
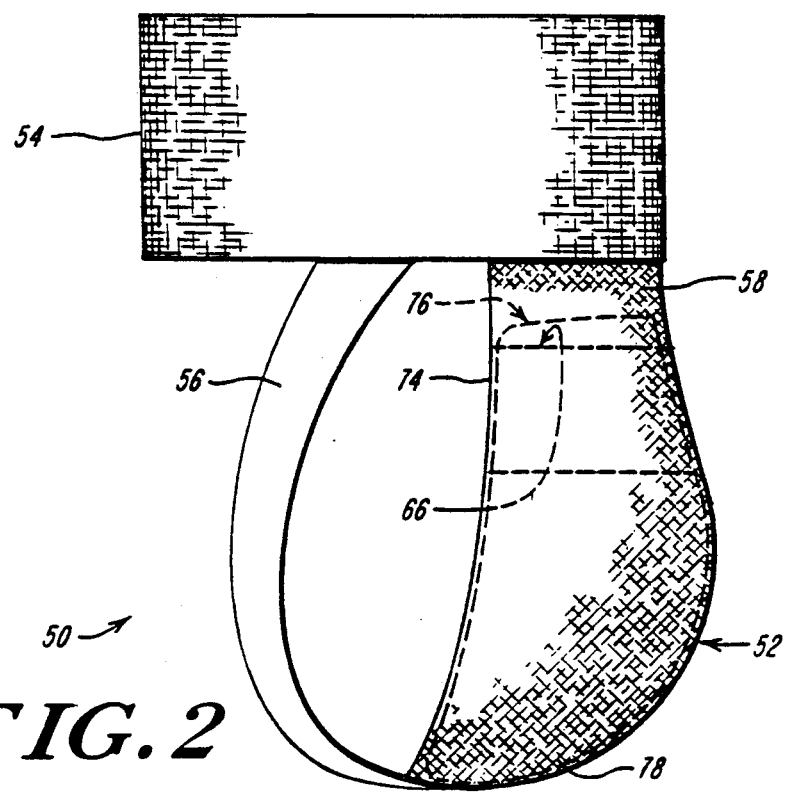
FIG. 2 is a side view of the embodiment of FIG. 1.

A first embodiment 50 of the athletic supporter according to the present invention, shown in FIG. 1 and FIG. 2, includes a pouch 52 secured to an elastic waistband 54 including supplemental support straps 56 attached thereto to maintain the athletic supporter comfortably on the body of the user. The pouch 52 has a front and rear panel, 58 and 60, respectively, of woven, non-woven, felt or knit material substantially continuously joined at the sides 62 and 64, and an aperture 66 at or near the top edge 68 The pouch includes a section 70 formed from a continuation of the front panel 60 which covers the aperture 66, partially overlapping the rear panel 58 and being fastened thereto and to supporting strap 54 by top seam 72 and edge seams 74. A protector 76 is received by the pouch 52 between the front and rear panels 58 and 60 by lifting the overlapping flap 70 and being inserted through the aperture 66, which causes the pouch to distort. When worn, stress imposed on the pouch at the points where it joins the other elements of the athletic supporter causes the pouch to conform to an undistorted shape (as per the drawing), the protector 66 is retained within the pouch 52 despite the stresses imparted thereon by the motions of the user.

Figure 2A:
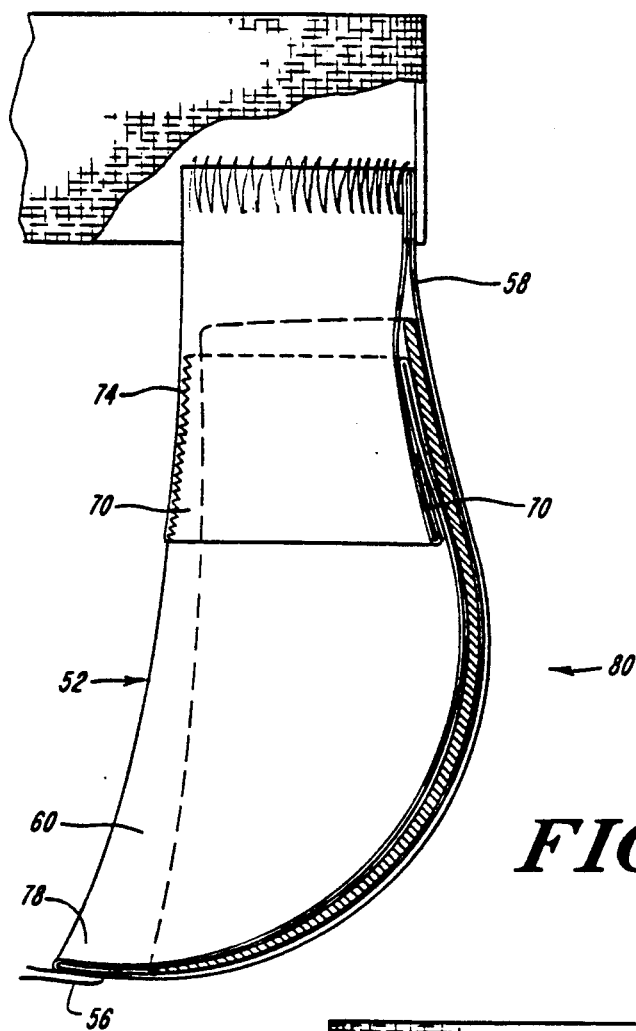
FIG. 2A is a cross section of the pouch of the athletic supporter of FIG. 2.

A side cross section view 80 is shown in FIG. 2A of the pouch 52, showing the front and rear panels 58 and 60, respectively, the overlapping flap 70 and the protector cup 76 retained therein. The auxiliary straps 56 are secured to the pouch 52 at a point 78 at the lower extremity of the pouch 52 and on the elastic support band 54, where appropriate.

Figure 3:
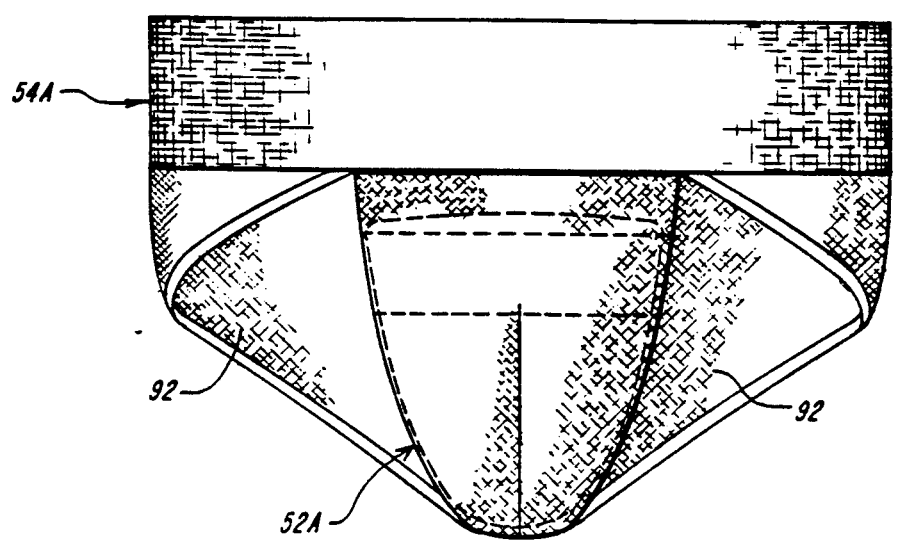
FIG. 3 is a front view of an alternate embodiment of the present invention.

In FIG. 3, an alternate embodiment 90 of the present invention shows a full seat panel 92 secured to the pouch 52A and to the elastic waistband 54A, providing more uniform support and distribution of stresses induced by the movement of the user.

Substitutions and modifications made by one skilled in the art are considered to be within the scope of the present invention, which is not to be limited except by the claims which follow.

What is claimed is:

1. For use with a protector cup, an athletic supporter comprising:
   a pouch adapter to receive said protector cup having an aperture through which said protector cup is received and an overlapping section of said pouch substantially covering said aperture and at least a portion of said pouch adjacent said aperture, said overlapping section being secured to said pouch at the periphery to said pouch; and
   means for supporting said pouch on the body of a user wherein
   the periphery of said overlapping section including a side edge thereof,
   said side edge overlapping section being permanently fastened to said pouch,
   said overlapping section is adapted to confront the body of said user, and
   stresses imparted on said pouch cause said overlapping section to retain said protector cup.

2. The athletic supporter of claim 1, wherein
   said pouch comprises edge portions, said aperture being disposed substantially at said edge portion.

3. The athletic supporter of claim 2, wherein said athletic supporter is worn by the user,
   said aperture is at an upper edge portion of said pouch and said overlapping section extends downward.

4. The athletic supporter of claim 1, wherein
   said means for supporting comprises an elastic band.

5. The athletic supporter of claim 1, wherein
   said pouch comprises one of a woven, non-woven, felt and knit material substantially entirely surrounding said protector cup.

6. An athletic supporter comprising
   a pouch having a front and a back panel joined at the periphery to include an unsecured panel edge having an aperture therein adapted to receive a protective device, said front panel extends beyond said unsecured panel edge and overlapping said back panel and permanently fastened thereto to substantially occlude said aperture to retain said protective device within said pouch; and means for supporting said pouch on the body of a user wherein the periphery of said overlapping section includes a side edge thereof, said side edge of said overlapping section being permanently fastened to said pouch said overlapping portion is adapted to confront the body of said user, 7. The athletic supporter of claim 6, wherein said front panel extends over said rear panel.

8. The athletic supporter of claim 6, wherein said edge is the top edge when the athletic supporter is worn by said user.

* * * * *